United States Patent
Kvasnik et al.

(10) Patent No.: US 7,435,601 B2
(45) Date of Patent: Oct. 14, 2008

(54) BIOLOGICAL SPECIMEN HANDLING METHOD

(75) Inventors: Michael Jeffrey Kvasnik, Plymouth, MN (US); Todd Richardson Fitz, Mound, MN (US)

(73) Assignee: Fitzco Incorporated, Spring Park, MN (US)

( * ) Notice: Subject to any disclaimer, the term of this patent is extended or adjusted under 35 U.S.C. 154(b) by 0 days.

(21) Appl. No.: 10/778,271

(22) Filed: Feb. 13, 2004

(65) Prior Publication Data

US 2004/0161855 A1    Aug. 19, 2004

Related U.S. Application Data

(60) Provisional application No. 60/448,294, filed on Feb. 19, 2003.

(51) Int. Cl.
C12M 1/22    (2006.01)
(52) U.S. Cl. .................. 436/165; 435/305.3; 435/305.4; 435/307.1
(58) Field of Classification Search .................. 422/61, 422/102; 435/288.3, 305.1, 305.3, 305.4, 435/307.1; 436/165
See application file for complete search history.

(56) References Cited

U.S. PATENT DOCUMENTS

| | | | | |
|---|---|---|---|---|
| 3,819,106 A | 6/1974 | Schuster | ...................... | 229/62 |
| 3,915,806 A | 10/1975 | Horlach | ...................... | 195/139 |
| 4,803,048 A | 2/1989 | Nason | ........................ | 422/58 |
| 5,415,282 A | 5/1995 | Kienholz | ..................... | 206/216 |
| 5,436,129 A | 7/1995 | Stapleton | ........................ | 435/6 |
| 5,484,731 A * | 1/1996 | Stevens | ................... | 435/305.3 |
| 5,674,456 A * | 10/1997 | Chess et al. | ................. | 422/102 |
| 5,807,527 A | 9/1998 | Burgoyne | .................... | 422/488 |
| 5,846,487 A | 12/1998 | Bennett, II | .................... | 422/58 |
| 5,856,102 A | 1/1999 | Bierke-Nelson et al. | ........ | 435/6 |
| 5,939,022 A | 8/1999 | Franciskovich | ............. | 422/100 |
| 5,939,259 A | 8/1999 | Harvey et al. | .................. | 435/6 |
| 5,981,293 A | 11/1999 | Charlton | ..................... | 436/177 |
| 6,168,922 B1 | 1/2001 | Harvey et al. | .................. | 435/6 |
| 6,171,260 B1 | 1/2001 | Hochmeister et al. | ....... | 600/572 |
| 6,176,371 B1 | 1/2001 | Tyrrell | ........................ | 206/204 |
| 6,291,171 B1 | 9/2001 | Ricciardi et al. | ............... | 435/6 |
| 6,299,842 B1 | 10/2001 | Kozak et al. | ................. | 422/102 |
| 6,357,583 B1 | 3/2002 | Rainen | ........................ | 206/205 |
| 6,423,536 B1 * | 7/2002 | Jovanovich et al. | ...... | 435/287.2 |
| 6,447,804 B1 | 9/2002 | Burgoyne | .................... | 424/488 |
| 2002/0007686 A1 | 1/2002 | Kozak et al. | ............. | 73/864.71 |
| 2002/0064776 A1 | 5/2002 | Liu et al. | ........................ | 435/6 |
| 2002/0068358 A1 * | 6/2002 | Campbell et al. | ........ | 435/289.1 |

(Continued)

FOREIGN PATENT DOCUMENTS

EP    0645447 A2    3/1995

(Continued)

*Primary Examiner*—Lyle A Alexander
(74) *Attorney, Agent, or Firm*—Michael A. Essien; Fondungallah Kigham & Essien, LLC (57) ABSTRACT

An apparatus for collecting, transporting and storing biological specimens. The apparatus includes a base having a tray portion for receiving the biological specimen and a lid operably connected to the base and moveable with respect to the base between a first closed position in which the tray portion is covered by the lid and a second open position wherein the tray portion is exposed for receipt or removal of the biological specimen.

8 Claims, 5 Drawing Sheets

U.S. PATENT DOCUMENTS

2003/0059347 A1 * 3/2003 Ostgaard et al. ............ 422/102

FOREIGN PATENT DOCUMENTS

| WO | WO 97/19337 | 5/1997 |
| WO | WO 00/76664 A1 | 12/2000 |
| WO | WO 01/30498 A1 | 5/2001 |
| WO | WO-01/67111 A2 * | 9/2001 |

* cited by examiner

BIOLOGICAL SPECIMEN HANDLING METHOD

RELATED APPLICATION

This application claims the benefit of a pending U.S. provisional application Ser. No. 60/448,294, filed Feb. 19, 2003, titled Biological Specimen Handling System, which is herein incorporated by reference.

BACKGROUND

Biological specimens, such as, for example, saliva, blood, DNA composites, recombinant DNA, and nucleic acids from organisms, must often be collected in the field or "at the scene" remote from suitable testing, archival, and/or analytical facilities while preserving the integrity of the specimens. The efficient collection, transportation and storage of such biological specimens become paramount, particularly where the analyses and results are used to solve crimes or are to be used in the prosecution of criminal offenses such as sexual assault, murder, drunk driving, etc. Other applications where the preservation of the integrity of samples during the collection, transporting and storage process is paramount include plant and animal sciences and other agriculture related fields, and environmental and public health fields, to name but a few.

Several systems have been developed or adopted to collect biological specimens, including pouches, envelopes, bottles, vials, and the like. Pouches and envelopes can be easily ripped, whereas bottles and vials are often clumsy or difficult to use when collecting samples. Other systems involve elaborate steps to preserve the specimens at the scene such as treating such specimens with, or immersing the specimens in, chemicals that may serve to retard the deterioration process. There are still other systems that require manually handling the specimen before testing. While these systems may serve their intended purpose, they are generally unsuitable for automated processes for analyzing collected biological specimens.

Accordingly, there is a need among forensic and law enforcement personnel, health care workers, parents, and others entrusted or charged with the responsibilities of obtaining, transporting and storing biological specimens for an apparatus and method that enables an efficient means to collect, transport, store, and retrieve the specimen in an effective, cost efficient system and wherein such a system can be used with automated processing systems. Such an apparatus and system is disclosed in the present invention.

SUMMARY

In one embodiment, the present invention provides an apparatus for handling a biological specimen. The apparatus includes a base and a lid; the base having a body portion and a tray portion with the tray portion adapted to receive a biological specimen. The lid is preferably operably connected to the base and is moveable between a first closed position in which the tray portion is covered and second open position in which the tray portion is exposed. In the preferred embodiment a matrix or substrate is removably disposed in the tray portion upon which the collected biological specimen is received.

The present invention also provides a system that is adaptable for use in manual and automated analytical systems. In automated systems, the present invention further provides a means to analyze the specimen without manual handling, thereby improving efficiency, enhancing safety and reducing the potential for contamination of the specimen. The apparatus may be used for short and long term storing biological specimen for later retrieval and analysis or for other purposes. The apparatus also preferably includes an identification label to identify the collected specimen and/or recording other pertinent information with respect to the collected specimen.

DETAILED DESCRIPTION

Figure 1:
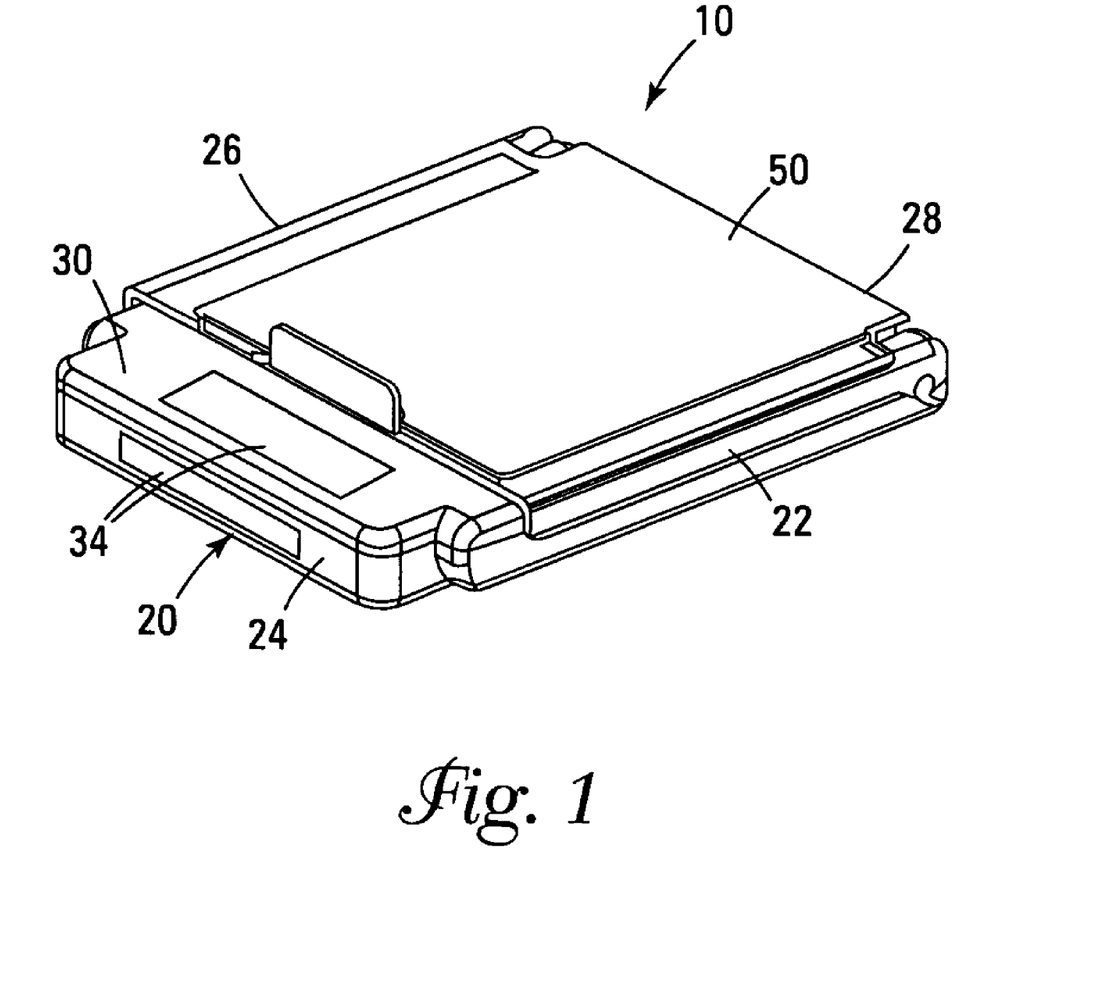
FIG. 1 is a perspective view of an embodiment of the biological specimen handling apparatus of the present invention shown in the closed position.
Figure 2:
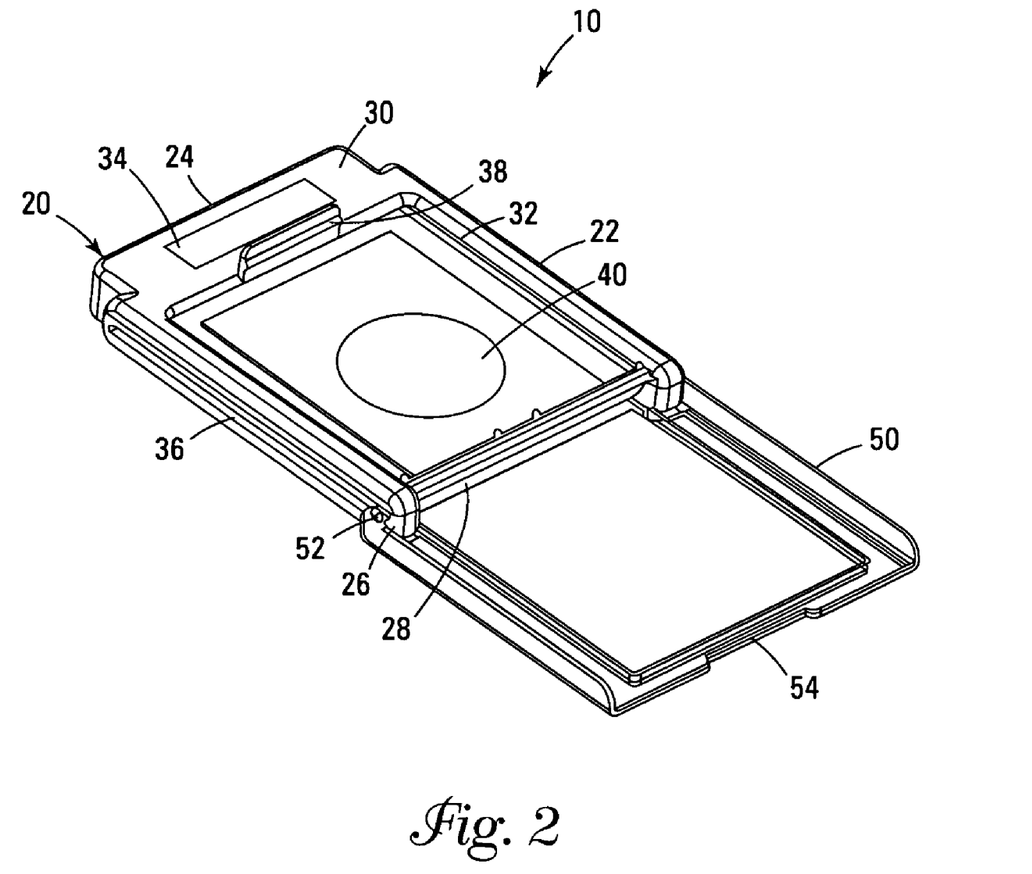
FIG. 2 is a perspective view of the apparatus of FIG. 1 in an open position.
Figure 3:
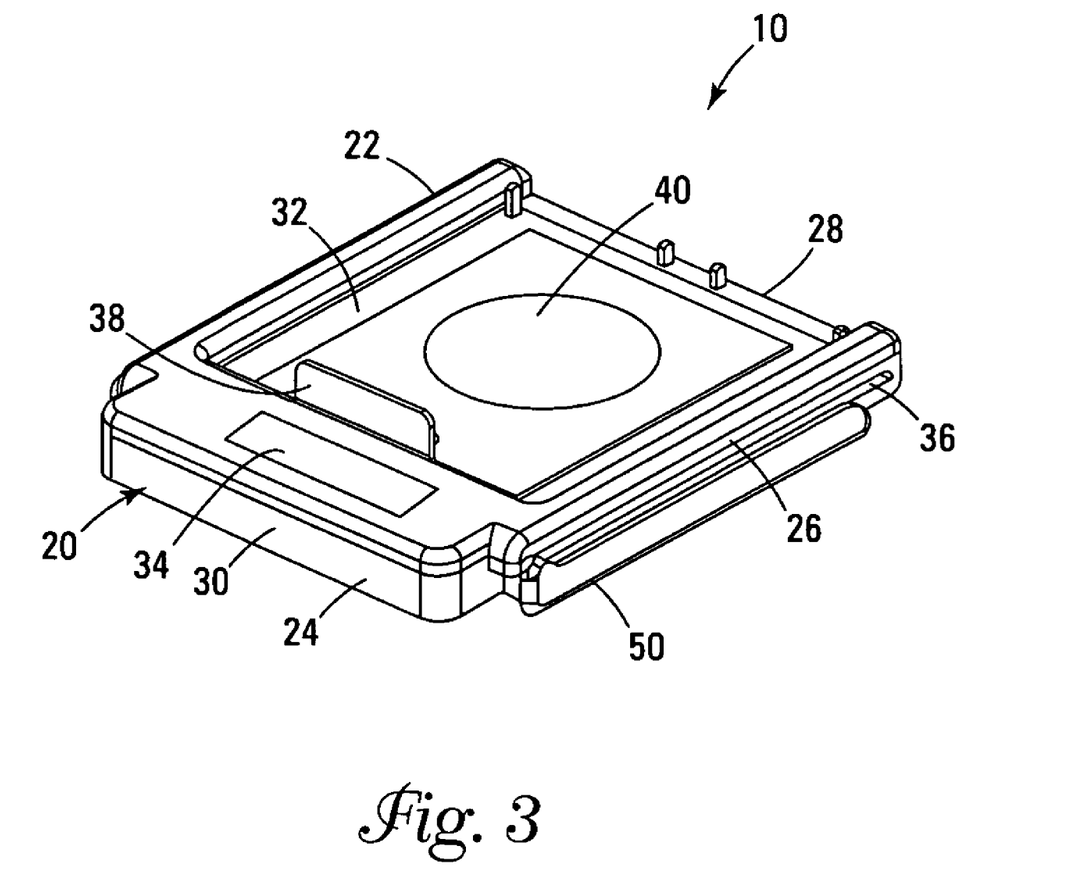
FIG. 3 is a perspective view of the apparatus of FIG. 1 in an open position showing the lid slid under the base.

FIGS. 1-3 illustrate a preferred embodiment of the present invention in the form of an apparatus 10 for handling biological specimens, such as, for example, saliva, blood, plasmids, DNA composites, recombinant DNA, nucleic acids from organisms, or any other biological specimen for which the integrity of the specimen is desired to be maintained throughout the collection, transportation, storage, and testing or analysis processes.

The apparatus 10 is preferably adapted for use in both manual and automated systems used in the analysis of biological specimens. Typical automated systems include Perkin-Elmer®, Beckman®, Tecan®, Wallach®, Packard®, and Hamilton®. As such, the apparatus 10 preferably has a "footprint" so as to accommodate a 96-well plate for automatic retrieval of the collected biological specimen. Typical 96well plate instruments are known to those skilled in the art.

The apparatus 10 preferably comprises a base 20 having a first end 22, a second end 24, a third end 26, a fourth end 28, and a body portion 30. The body portion 30 preferably includes a tray portion 32 (FIG. 2) for receiving a biological specimen (not shown). As discussed in greater detail later, the tray portion 32 preferably includes a matrix or substrate 40 upon which the collected biological specimen is received. The substrate 40 is preferably removably retained within the tray portion 32. The preferred embodiment of the present invention also includes a lid 50 that is operably connected to the base 20 and usable, in part, as a cover over the tray portion 32, and thereby over the specimen, so as to prevent or reduce the risk of contamination of the collected specimen during transportation and storage.

Best illustrated in FIG. 3, the tray portion 32 is preferably sunken or below the top surface level of the body portion 30 of the base 20 so as to form a pocket in the body portion 30. This sunken tray portion or pocket 32 allows the collection of larger biological samples while still allowing the lid 50 to close over the tray portion 32.

Although FIGS. 1-3 show the base 20 as being substantially rectangular, it should be appreciated that the base 20 may be any desired shape, including square, circular, oval or any other shape. Additionally, the base 20 may be formed from a single or multiple pieces of material, and may be made of any desired material capable of receiving and holding a desired biological specimen. If the base is comprised of a combination of multiple pieces, it is desirable to ensure the combination of pieces are securely connected together by any well known means to prevent premature dismantling during use, or other unintended results.

As previously identified, the tray portion 32 preferably includes a matrix or substrate 40 that is suitable to receive the collected biological specimen for storage, analysis and/or testing. The substrate 40 is preferably removable from the tray portion 32 so as to enable easier collection of the biological sample onto the substrate 40, and/or to enable easier retrieval of the collected biological sample for testing or analysis without having to physically or manually handling the biological specimen. Although preferably remaining removable, the substrate 40 may have an adhesive on one side, preferably along the edges of the lower portion of the substrate 40 to facilitate placement of the substrate 40 on the tray portion 32 for collection of the specimen and to prevent the substrate from inadvertently falling out of the tray portion 32 during or after collecting the specimen. Such adhesive is preferably located on portions of the substrate 40 such that it will not contaminate the specimen during collection and/or retrieval for analysis or affect the placement of the specimen on the substrate 40. Additionally, the substrate 40 may be adapted to include a handle or means of handling, such as a tab, flag, or the like (not shown) that may be used for easier grasping of the substrate 40 to facilitate insertion into or removal from the tray portion 32 of the base 20.

Different materials may be used for the substrate 40 depending on the specimen to be collected or other controlling factors. For example, the substrate may comprise such materials as sponge, cellulose based papers (for example, cellulose, nitrocellulose or carboxymethylcellulose papers), glass, filter paper, cotton paper, nylon, chemically treated papers, hydrophilic polymers (for example, polyamide, polyester, carbohydrate polymers) polytetrafluroethylene, fiberglass, porous ceramics, and the like.

As previously discussed, after the specimen is collected and it is desired to test or analyze the collected specimen, the substrate 40 is preferably removable from the base 20 so as to more readily enable the retrieval of the collected specimen for analysis or testing. The collected sample received upon the substrate may then be cored, or, alternatively, the sample may be punched through the substrate or analyzed intact, i.e., by removal of the specimen from the substrate 40 without the added step or process of coring or punching. A coring process removes only that portion of the specimen needed for evaluations without boring a hole through the substrate. The cored specimen may then used for the intended evaluation. A punching process punches through a portion of the specimen and substrate, typically a small circle. The punched specimen is then retrieved for use in the desired evaluation. Given that very small sample sizes are required for testing typical biological specimen (about 0.5 to 10 millimeters in diameter), the substrate 40 is preferably adapted to be dropped via an automated punch-through process to a receptacle usable to perform the automated analysis of the collected specimen.

The substrate 40 may have an identification label or tag associated with it to provide a means of identifying the specimen collected. Additionally, or in the alternative, one end 22, 24, 26, 28 of the base 20 may be used to receive an identification label or tag 34 (FIGS. 2 and 3) to identify the specimen collected. The identification label or tag 34 may simply include a blank label that can be written upon with pen or other writing instrument, or the identification instrument 34 may include bar codes or other computer readable means of identifying the collected specimen and or other relevant data.

The lid 50 is moveable between a first closed position (FIG. 1) and a second open position (FIG. 2). To the accomplishment of the foregoing, the lid 50 may be removably detachable from the base 20. Preferably, however, the lid 50 is hingedly connected at one end of the base 20. In the preferred embodiment of FIG. 2, the lid 50 is shown hingedly connected to the base 20 at the fourth end 28 by pins 52 on either side 22, 26 of the base. Furthermore, as best illustrated in FIG. 3, in addition to being hingedly connected to the base 20 by pins 52, the first and third ends 22 and 26 of the base 20 also preferably include grooves 36 along which the pins 52 are free to slide, thereby enabling the lid 50 to be slidably moved from the fourth end 28 toward the second end 24 below the base 20. The second end 24 of the base 20 preferably includes a latch mechanism 38 such as a projecting resilient detent that engageably receives an edge 54 of the lid 50.

The lid 50 of the apparatus may be opaque, transparent or translucent. Depending on the application, an opaque lid may be desirable if the specimen may degrade or otherwise change in character if exposed to light. A transparent lid or a lid that provides a user with the ability to view the collected specimen or read the identification instrument through the lid may be beneficial if it is desirable to be able to identify or otherwise obtain information about the collected sample without having to open the lid.

Figure 4:
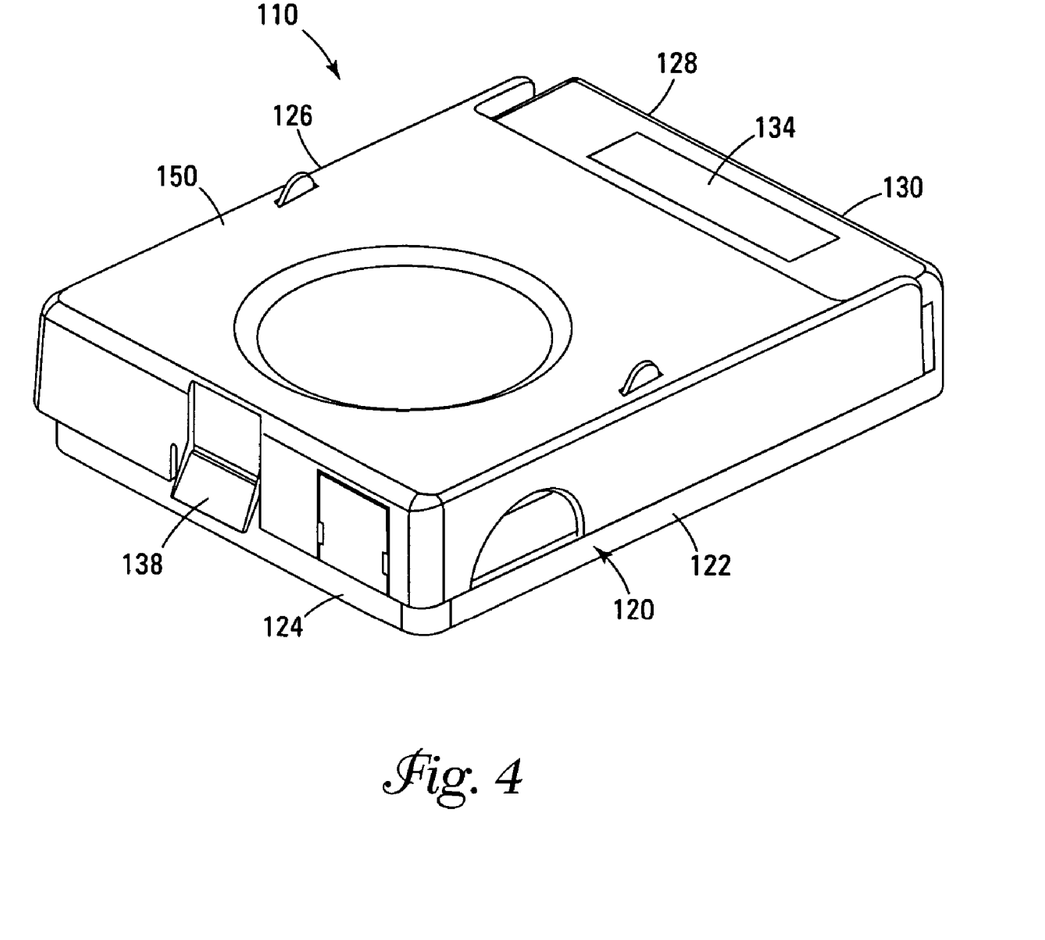
FIG. 4 is a perspective view of another embodiment of the biological specimen handling apparatus of the present invention shown in the closed position.
Figure 5:
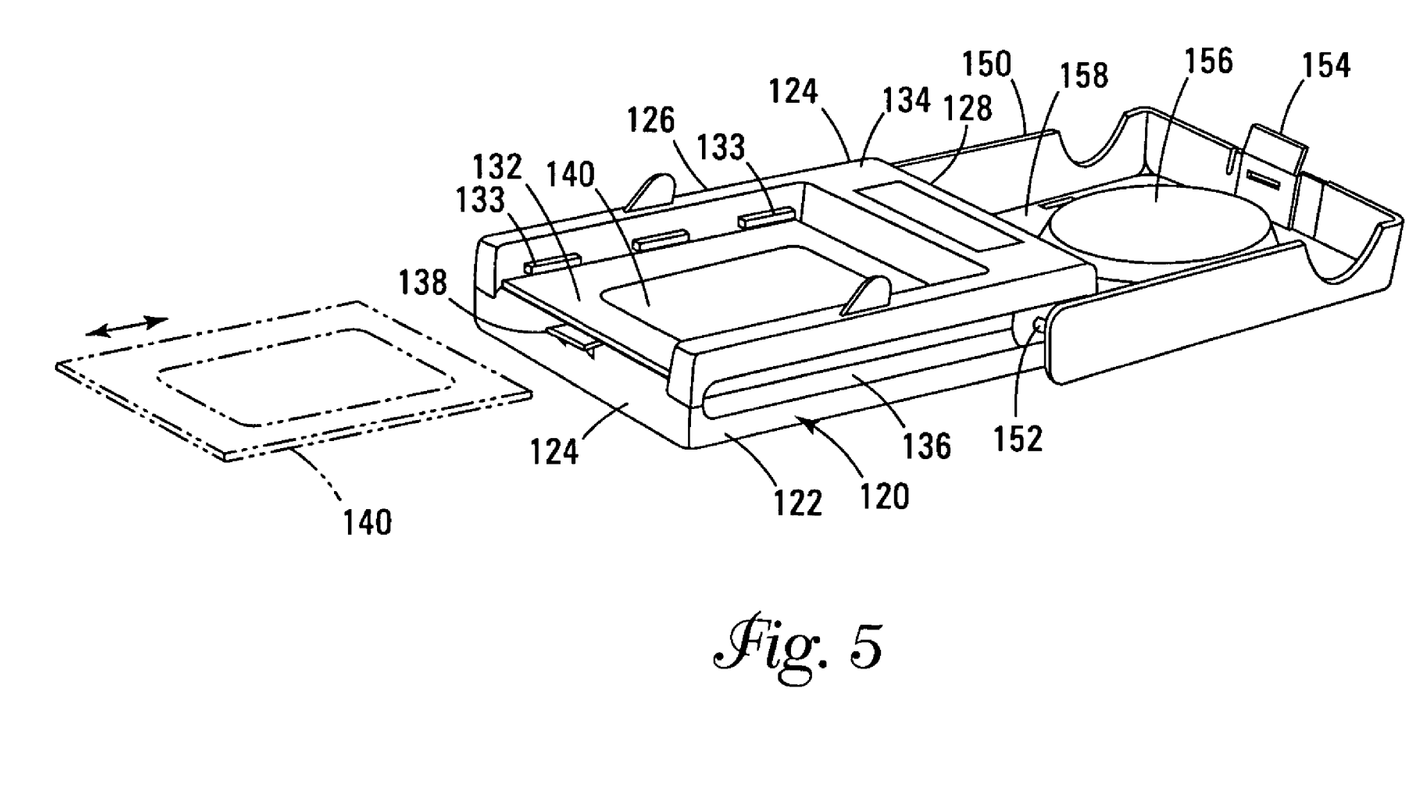
FIG. 5 is a perspective view of the apparatus of FIG. 4 in an opened position.

FIGS. 4 and 5 disclose another embodiment of the apparatus 110 of the present invention. As with the previous embodiment 10, the apparatus 110 comprises a base 120 having a tray portion 132 within which collected biological specimens are received, and a lid 150 moveable between a first closed position covering the tray portion (FIG. 4) and a second open position in which the tray portion is exposed (FIG. 5).

As with the above-described apparatus 10, the apparatus 110 is preferably adapted for use in both manual and automated systems used in the analysis of biological specimens, and therefore, preferably has a footprint so as to accommodate a 96well plate for automatic retrieval of the collected biological specimen. the apparatus 110 may be made in any desired shape and from a single or multiple pieces of any desired material suitable for collecting, transporting and storing biological specimens.

The base 120 is preferably substantially rectangular, having a first end 122, a second end 124, a third 126, and a fourth end 128. As best illustrated in FIG. 5, as with the apparatus 10, the tray portion 132 of apparatus 110 preferably includes a matrix or substrate 140 upon which the collected biological specimen is received. The substrate 140 is preferably removable from the tray portion 132 as illustrated by phantom lines in FIG. 5. In the embodiment of FIG. 5, the tray portion 132 includes a projections 133 forming a groove or slot to slidably receive the substrate 140.

Similar to the previously described embodiment 10, the lid 150 of apparatus 110, is preferably hingedly connected to the base 120 at one end by pins 152, the first and third ends 122 and 126 of the base 120 also preferably include grooves 136 along which the pins 152 are free to slide, thereby enabling the lid 150 to be slidably moved from the fourth end 128 toward the second end 124 below the base 120. The second end 124 of the base 120 preferably includes a latch mechanism 138 such as a projecting resilient detent plate that engageably receives an edge 154 of the lid 150. Also, as with the previously described embodiment 10, the lid 150 of apparatus 110 may be opaque, transparent or translucent depending on the application.

As best illustrated in FIG. 5 the lid 150 preferably includes a raised surface 156 projecting upwardly from the underside 158 of the lid 150. This raised surface 156 preferably overlays the specimen location on the substrate 140 and ensures the proper placement and transfer of the specimen onto the substrate 140 when the lid 150 is in a closed position. Additionally, this raised surface 156 acts to push or force the specimen onto the substrate 140 when the lid 150 is closed, thus enhancing the absorption (where necessary) of the biological specimen onto the substrate 140.

As with the above-described apparatus 10, the retrieval of the collected biological specimen from the apparatus 110 for analysis or testing may be accomplished by coring the specimen from the substrate 140 or punching out a portion of the specimen for analysis or with the specimen and substrate 140 intact.

In use, the lid 50, 150 of the apparatus 10, 110 is preferably opened as shown in FIGS. 2 and 5, respectively, thereby exposing the tray portion 32, 132 within which is preferably disposed and an appropriate matrix or substrate 40, 140 for receiving the biological specimen to be collected. By way of example, buccal cells may be collected from the oral cavity of an individual using a swab, spatula or any other means as is known in the art. This swab containing the buccal cell sample is then rubbed on the exposed substrate 40, 140 to transfer the specimen onto the substrate 40, 140. The lid 50, 150 is subsequently closed and secured by the latch mechanism 38, 138 to prevent contamination of the collected specimen. An identification label or tag 34, 134 may then be placed or incorporated into the substrate 40, 140 or placed on the body portion 30, 130 of the base 20, 120 to ensure proper identification of the specimen and/or to record other relevant or desired data concerning the specimen.

As identified above, the collection of the specimen is preferably accomplished without manually handling the specimen, thus preventing contamination or introduction of foreign elements. Similar or modified processes may be incorporated depending on the specimen to be obtained, such as skin scrapes, samples from crime scenes, alcohol-related or driving-while-impaired (DWI) evidence, research samples, and the like. The present invention is especially practical in the collection of blood samples wherein the blood sample is obtained (typically with a syringe) from the subject and delivered (deposited, injected, sprayed) onto a desired area on the substrate 40, 140. The closed apparatus 10, 110 containing the collected biological specimen may then be safely and conveniently transported to a suitable location, such as a laboratory, a testing facility, storage or archival facility, or the like.

The testing or analysis of the collected biological specimen may be accomplished by presenting the apparatus 10, 110 to the appropriate personnel, or to a robotic and/or automated biological specimen analysis system. The lid 50, 150 of the apparatus 10, 110 is then opened to expose the collected biological specimen. Depending on the specimen and the retrieval method to be used, the substrate 40, 140 may removed from tray portion 32, 132 for coring, punching processes or the sample and substrate may remain intact. A coring process may not require the substrate to be removed or extended outside the base 20, while a punching system may require such removal or extension. Additionally, as discussed above, the entire substrate 40, 140 may be removed and assayed, archived or stored intact with the collected specimen.

The present invention provides a convenient and efficient specimen storage or retention system. After collection of the needed biological specimen, the apparatus 10, 110 may be stored on a rack, shelf, drawer, and the like. The apparatus 10, 110 is preferably stackable, and may provide for easy labeling of the identity of each specimen (bar codes, numbers, names, etc.) for efficient retrieval.

Accordingly, the present invention provides a system that is easy to use in the collection, retention and transportation of biological specimens. With the present system, there is no particular need to store the swab or other collection instrument. However, if desired, the collection instrument may be retained along with the collected specimen within the tray portion 32, 132 of the apparatus 10, 110. Further, the collection apparatus and the substrate can be adaptable to suit specific circumstances or events, such as directly depositing or applying the specimen to the substrate 40, 140.

Another benefit of the present invention is the provision of an apparatus that is easy to handle, allows for the easy and quick retrieval of the substrate, and can be stored, for example, in a cassette-type handling system. The apparatus of the present invention is easily transportable and may be tracked as needed when in transit. This is especially important to law enforcement and judicial system in tracking and determining "chain of custody" issues, among others. Bar codes or other suitable tracking aid may be placed on the edges of the apparatus for computer or other electronic equipment based identification. This may provide a time-and-date stamp upon collection, as automatic and real-time recording of sampling is now practical.

Having thus described the preferred embodiments of the present invention, those of skill in the art will readily appreciate that the teachings found herein may be applied to yet other embodiments within the scope of the claims hereto attached.

What is claimed:

1. A method of handling a biological specimen, the method consisting of:
   providing an apparatus for handling a biological specimen via a 96-well plate, the apparatus adaptable to accommodate a 96-well plate and having a grooved base, the grooved base having a body portion and a tray portion adapted for receiving a biological specimen, and a slidably movable lid operably connected to the grooved base and moveable between a first closed position and a second open position, wherein the slidably movable lid is hingedly connected to and slidably movable about the grooved base, further wherein the lid is slidable under the base by means of the groove;
   collecting a biological specimen at a first location;
   moving the slidably movable lid of the apparatus from the first closed position to the second open position, wherein the slidably movable lid is hingedly connected to and slidably movable about the base;
   placing the collected biological specimen in an exposed tray portion of the apparatus;
   moving the hingedly connected lid from the second open position to the first closed position; providing an identification to the apparatus containing the biological specimen; and
   transporting the apparatus to a second location, wherein the chain of custody of the biological specimen is traceable.

2. The method of claim 1, wherein the tray portion includes a substrate.

3. The method of claim 2, wherein the substrate is removable from the base.

4. The method of claim 1, wherein the base includes an identification label.

5. The method of claim 4, wherein the identification label includes a label identifying the collected specimen.

6. The method of claim 5, wherein the label includes a computer readable code.

7. The method of claim 1, wherein the second location is a testing facility.

8. The method of claim 1, wherein the second location is a storage facility.

* * * * *